United States Patent
Adell

(10) Patent No.: US 10,011,399 B1
(45) Date of Patent: Jul. 3, 2018

(54) FABRICATION OF POLYMERIC DENTAL DEVICES AND AIDS

(71) Applicant: Loren S. Adell, Sunnyvale, TX (US)

(72) Inventor: Loren S. Adell, Sunnyvale, TX (US)

(73) Assignees: Loren S. Adell, Sunnyvale, TX (US); Michael Adell, Sunnyvale, CA (US)

( * ) Notice: Subject to any disclaimer, the term of this patent is extended or adjusted under 35 U.S.C. 154(b) by 301 days.

(21) Appl. No.: 14/712,929

(22) Filed: May 15, 2015

(51) Int. Cl.
| | |
|---|---|
| *B65D 35/24* | (2006.01) |
| *B05C 17/005* | (2006.01) |
| *B65B 3/04* | (2006.01) |
| *B65B 51/10* | (2006.01) |
| *B65B 43/02* | (2006.01) |
| *B65D 17/50* | (2006.01) |
| *B65D 77/06* | (2006.01) |
| *B65D 35/22* | (2006.01) |
| *B65D 77/08* | (2006.01) |
| *B29C 65/72* | (2006.01) |
| *B29C 65/76* | (2006.01) |
| *A61K 6/00* | (2006.01) |

(52) U.S. Cl.
CPC .............. *B65D 35/242* (2013.01); *A61K 6/00* (2013.01); *B05C 17/00563* (2013.01); *B29C 65/72* (2013.01); *B29C 65/76* (2013.01); *B65B 3/04* (2013.01); *B65B 43/02* (2013.01); *B65B 51/10* (2013.01); *B65D 17/50* (2013.01); *B65D 35/22* (2013.01); *B65D 35/24* (2013.01); *B65D 77/06* (2013.01); *B65D 77/08* (2013.01)

(58) Field of Classification Search
CPC ........ B65D 77/08; B65D 77/06; B65D 35/24; B65D 35/242; B65D 35/22
See application file for complete search history.

(56) References Cited

U.S. PATENT DOCUMENTS

| | | | | | |
|---|---|---|---|---|---|
| 2,176,923 | A | * | 10/1939 | Nitardy | B65D 35/22 206/221 |
| 3,294,227 | A | * | 12/1966 | Schneider | B65D 81/3266 206/219 |
| 3,608,709 | A | * | 9/1971 | Pike | B29C 65/76 206/219 |
| 3,736,933 | A | * | 6/1973 | Szabo | A61M 5/002 206/366 |
| 4,849,213 | A | * | 7/1989 | Schaeffer | A61K 8/042 424/53 |
| 5,154,321 | A | * | 10/1992 | Shomer | B01F 5/0683 206/219 |
| 5,169,030 | A | * | 12/1992 | Lewin | B65D 35/22 222/107 |

(Continued)

*Primary Examiner* — Benjamin A Schiffman
(74) *Attorney, Agent, or Firm* — George L. Boller

(57) ABSTRACT

A hermetically sealed enclosure for use in fabricating a polymeric dental article. Monomers are mixed within the enclosure by squeezing a first burst pouch to break a first burst seal between it and a second burst pouch and manipulating the enclosure by hand to initiate a polymerization reaction while the enclosure remains hermetically sealed. A second burst seal between the second burst pouch and a dispensing funnel chamber is broken by further squeezing which forces the mixture into the dispensing funnel chamber. The mixture is dispensed from an outlet of the dispensing funnel chamber by further squeezing after a tear-off strip closing the outlet has been torn off.

7 Claims, 10 Drawing Sheets

(56) References Cited

U.S. PATENT DOCUMENTS

| | | | | |
|---|---|---|---|---|
| 5,171,813 A * | 12/1992 | Patel | B65D 81/32 526/227 |
| 5,244,121 A * | 9/1993 | Shomer | B01F 5/0683 206/219 |
| 5,284,275 A * | 2/1994 | Shomer | B01F 5/0683 206/219 |
| 5,928,213 A * | 7/1999 | Barney | A61J 1/10 206/219 |
| 6,036,005 A * | 3/2000 | Krause | B65D 35/242 206/221 |
| 6,379,069 B1 * | 4/2002 | May | B65D 25/08 222/490 |
| 6,641,319 B2 * | 11/2003 | May | B65D 25/08 264/328.12 |
| 6,869,242 B2 * | 3/2005 | May | B65D 25/08 222/490 |
| 7,097,075 B2 * | 8/2006 | Peuker | B65D 81/3294 206/221 |
| 7,132,462 B2 * | 11/2006 | Lehmann | A61K 6/083 433/226 |
| 8,376,183 B1 * | 2/2013 | Rosen | B65D 75/5811 222/1 |
| 8,968,000 B2 * | 3/2015 | Leiner | A61O 5/062 433/87 |
| 2002/0012563 A1 * | 1/2002 | May | B65D 25/08 401/132 |
| 2004/0146334 A1 * | 7/2004 | May | B65D 25/08 401/132 |
| 2005/0028863 A1 * | 2/2005 | May | B65D 25/08 137/68.19 |
| 2007/0114144 A1 * | 5/2007 | Suzuki | B65D 81/3266 206/219 |
| 2007/0119862 A1 * | 5/2007 | Backes | B65D 1/095 222/94 |
| 2008/0306168 A1 * | 12/2008 | Craig | A61K 6/0017 514/772.4 |
| 2011/0132782 A1 * | 6/2011 | Ilfrey | B65D 81/3266 206/222 |
| 2015/0043838 A1 * | 2/2015 | Jaouen | A45D 34/00 383/38 |
| 2015/0246766 A1 * | 9/2015 | Wolf | B65D 35/22 222/145.5 |

\* cited by examiner

FABRICATION OF POLYMERIC DENTAL DEVICES AND AIDS

FIELD OF THE INVENTION

This invention relates to the fabrication of polymeric dental devices and aids such as dental arch models and to a product for use in performing the fabrication process.

BACKGROUND OF THE INVENTION

Polyurethane is an example of a polymer which is synthesized by condensation reaction of fluid monomers in a vessel. During the reaction process, different molecular groups react with each other to chemically link, and they in turn link with other monomers to form even larger molecules. Once the original reactants have been mixed, the on-going reaction continues to have fluidity until the reaction concludes with a sudden transformation of the mixture into a solid of high molecular weight.

In the practice of dentistry, which includes general dentistry and related specialties, the above-described process is used to fabricate certain dental devices and dental aids. For example, an impression of a person's dental arch can provide a cavity into which an on-going reaction of reactants is introduced. When the reaction concludes, the result is a solid polymeric model of the person's dental arch which when removed from the impression can be used as needed.

Preparation of a mixture of reactants requires care in accurately measuring the quantity of each reactant to be used. Failure to measure the proper quantity of each reactant may result in an imperfect finished product which cannot be used and becomes waste because the process is not reversible.

A further factor in the process is length of time available before a reaction concludes. Because the reaction commences with mixing of the reactants, a limited time exists until the reaction concludes. A person preparing a mixture of monomers first performs their mixing in a vessel and once the reactants have been sufficiently mixed, pours the mixture into a form such as an arch impression. Failure to complete the pour before the mixture solidifies will not produce the desired result. Furthermore, if air bubbles are present in the pour, sufficient time to puncture them before solidification of the mixture may not be available.

SUMMARY OF THE DISCLOSURE OF THE INVENTION

The process which has been described above is rather labor-intensive, is subject to human error, and if not practiced with due care, generates waste in terms of both product and time.

Briefly, this disclosure introduces a hermetically sealed enclosure comprising flexible front and back plastic sheets joined together to create a first burst pouch for hermetically enclosing a first monomer, a second burst pouch for hermetically enclosing a second monomer, and a first burst seal separating the two burst pouches. A second burst seal separates the second burst pouch from a dispensing funnel chamber. With each burst pouch hermetically sealing a respective monomer, the first burst pouch is externally squeezed by hand to break the first burst seal and force some of the first monomer into the second burst pouch thereby initiating the polymerization process. The sheets have transparency which allows the mixture to be seen. The first and second burst pouches are squeezed and manipulated to thoroughly mix the two reactants, while forcing the mixture largely into the second burst pouch but without breaking the second burst seal. For example, the flexibility of the sheets allows them to be rolled up to largely collapse the first burst pouch and force the mixture into the second burst pouch. With the first burst pouch largely collapsed, increased pressure applied externally to the second burst pouch causes the second burst seal to break and force at least some of the mixture into the dispensing funnel chamber as the second burst pouch collapses. The enclosure continues to hermetically seal the mixture although the reaction has started. With the mixture having been forced into the dispensing funnel chamber, a tear-off strip at an end of the enclosure is torn off to open an outlet of the dispensing funnel chamber. Further squeezing of the mixture in the second burst pouch and dispensing funnel chamber forces mixture out of the enclosure through the outlet of the dispensing funnel chamber. Squeezing is continued until substantially all of the mixture, or a lesser quantity if desired, has been dispensed. When the process concludes, the dispensed mixture becomes a solid polymer.

As applied to the creation of various dental devices and dental aids, the enclosure and method of its use can make the process easier, more efficient, and less wasteful of time and materials.

The foregoing summary is accompanied by further detail of the disclosure presented in the Detailed Description below with reference to the following drawings which are part of the disclosure.

DETAILED DESCRIPTION

Figure 1:
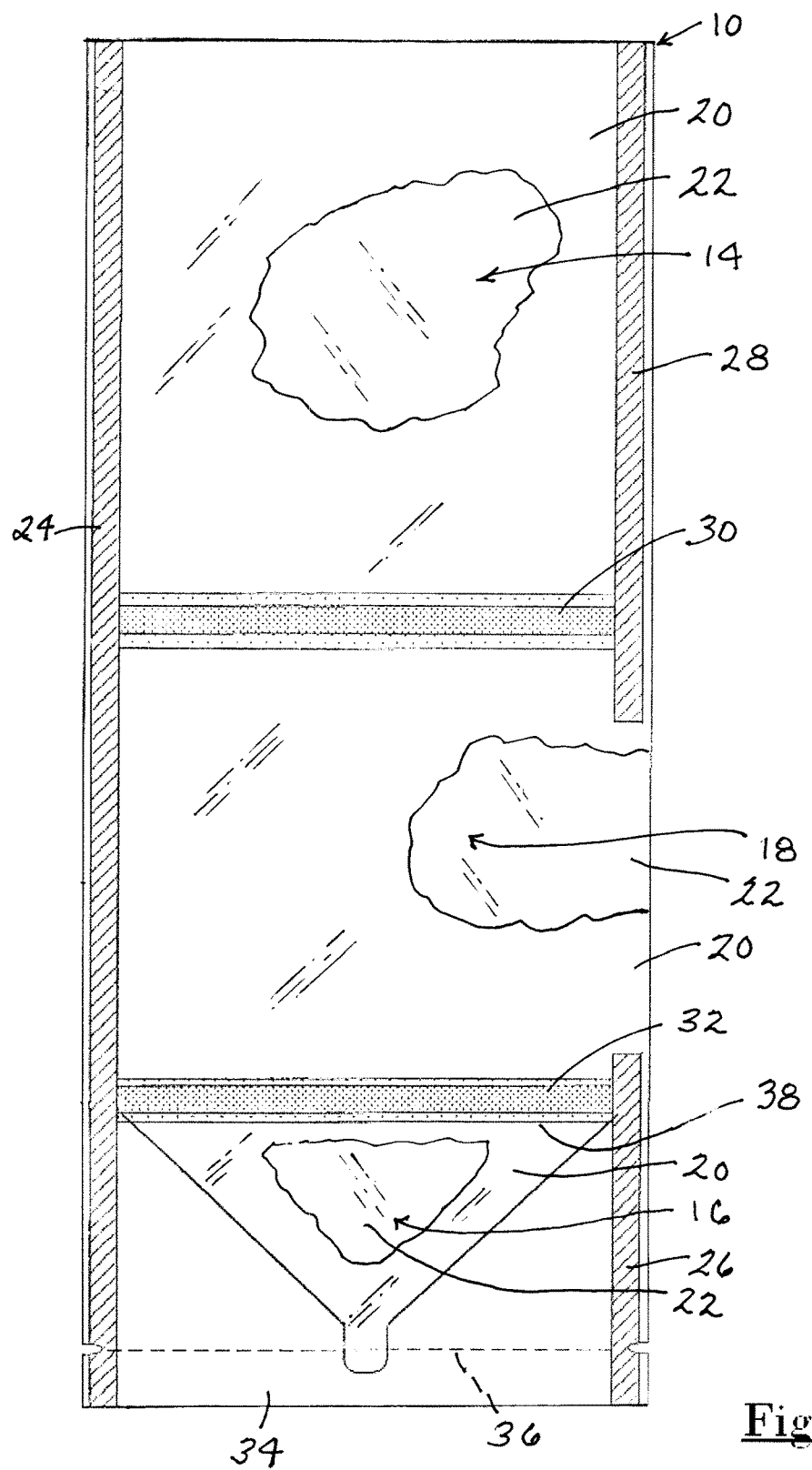
FIG. 1 is a front view of a product which is used to make a hermetically sealed enclosure, certain portions being broken away for the purpose of illustration.
Figure 3:
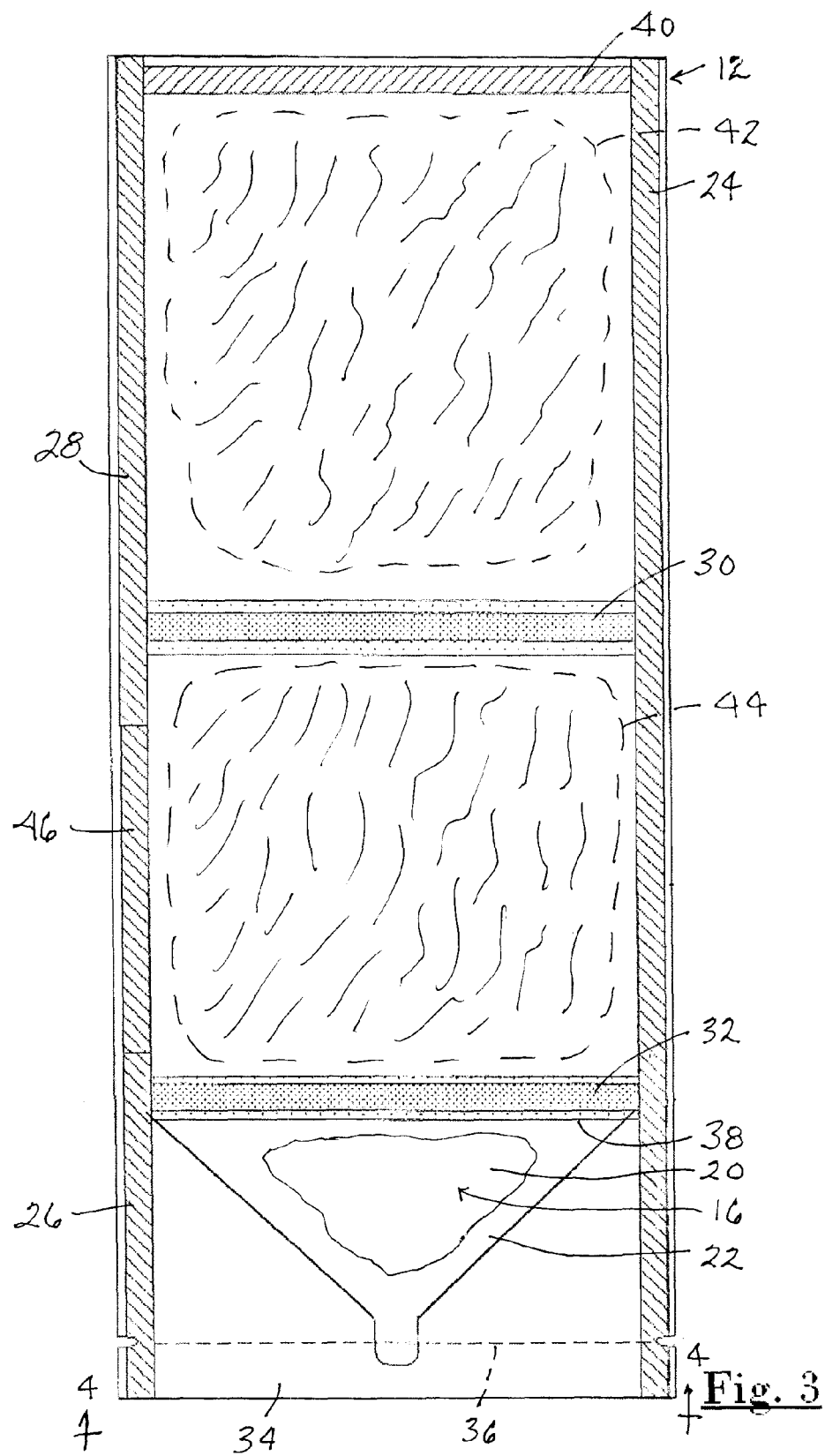
FIG. 3 is a view similar to FIG. 2 after having been filled with monomers, showing the hermetically sealed enclosure ready for use.

FIG. 1 shows a product 10 for use in creating a hermetically sealed enclosure 12, shown in FIG. 3, having a first burst pouch 14 at one lengthwise end, a dispensing funnel chamber 16 at the opposite lengthwise end, and a second burst pouch 18 in the middle.

As will be explained with reference to FIG. 3 and later Figs., first burst pouch 14 contains a first monomer, and second burst pouch 18 contains a second monomer. The two monomers are reaction polymers which when mixed together initiate a polymeric reaction leading to the fabrication of a solid polymer, such as polyurethane, at the reaction's conclusion.

Figure 2:
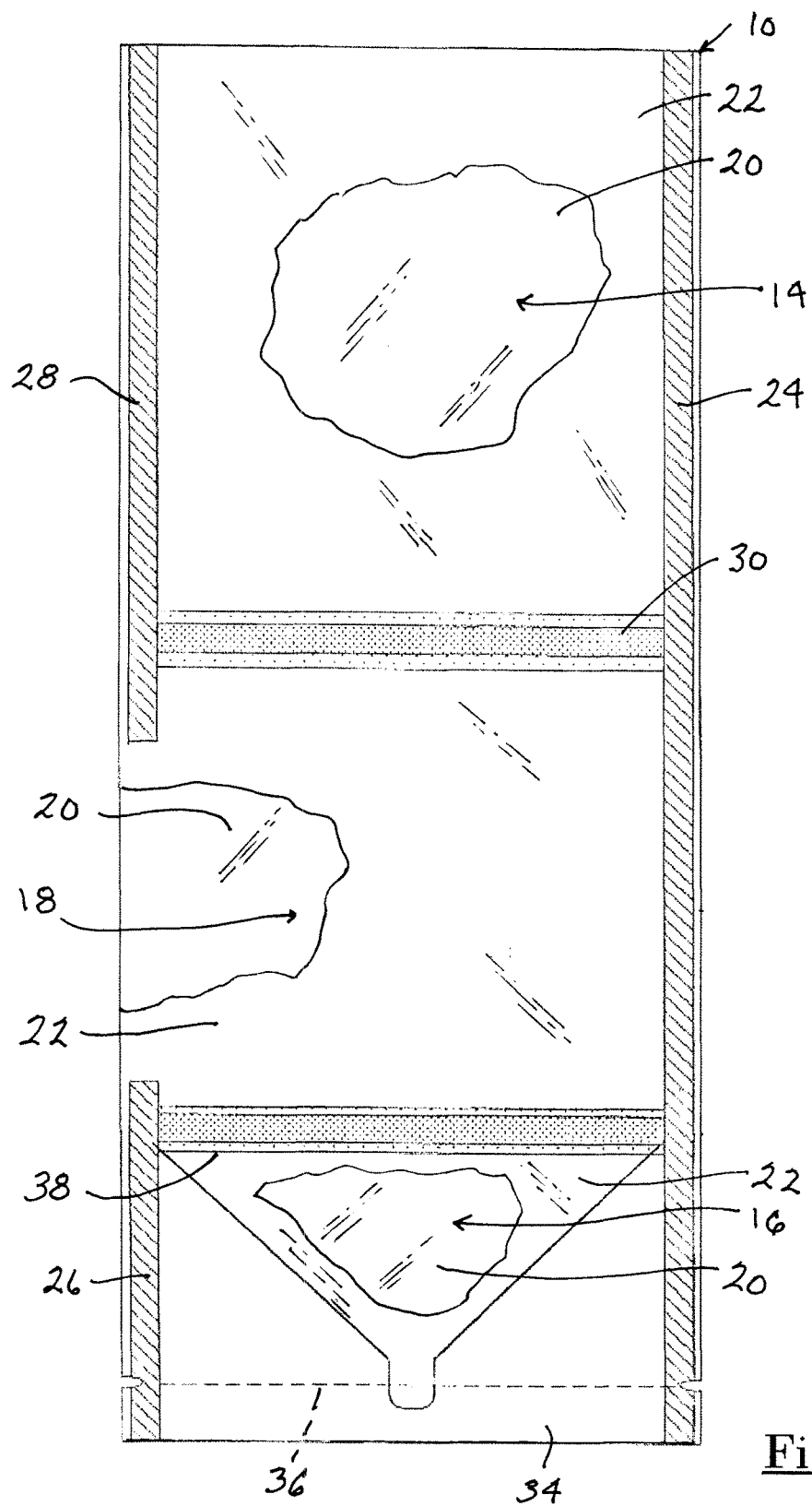
FIG. 2 is a back view of FIG. 1, also with certain portions being broken away for the purpose of illustration.

As shown in FIGS. 1 and 2, product 10 is unfilled with either monomer and comprises a flexible plastic front sheet 20 and a flexible plastic back sheet 22. An example of a suitable material for the sheets is polyethylene. The sheets themselves may comprise one or more layers in addition to a polyethylene layer. An example of one such additional layer is an EVOH layer which forms a barrier to certain gases to which polyethylene alone may not provide the best barrier. Such multi-layer sheets may be fabricated by a co-extrusion process. Both sheets 20, 22 are transparent and have essentially congruent rectangular perimeter margins which are sealed together as follows.

With reference to FIG. 1, a first side seal 24 is created between front sheet 20 and back sheet 22 along the entire length of the left perimeter margin of product 10 by heat sealing the sheets together. A second side seal 26 is created between front sheet 20 and back sheet 22 along a first portion of the length of the right perimeter margin of product 10 by heat sealing the sheets together. A third side seal 28 is created between front sheet 20 and back sheet 22 along a second portion of the length of the right perimeter margin of product 10 by heat sealing the sheets together. In this way, the left perimeter margins of first burst pouch 14, second burst pouch 18, and dispensing funnel chamber 16, and the right perimeter margins of first burst pouch 14 and dispensing funnel chamber 16 are sealed.

A frangible first burst seal 30 is disposed between front sheet 20 and back sheet 22 and is sealed to both sheets and to side seals 24 and 28, thereby sealing the lengthwise inner end of first burst pouch 14 which is adjacent one end of second burst pouch 18. A frangible second burst seal 32 is disposed between front sheet 20 and back sheet 22 and is sealed to both sheets and to side seals 24 and 26, thereby sealing the lengthwise end of second burst pouch 18 which is adjacent dispensing funnel chamber 16. Front sheet 20 and back sheet 22 are sealed to each other and to side seals 24 and 26 to close dispensing funnel chamber 16 such that the portions of sheets 20 and 22 which form the dispensing funnel chamber are not sealed to each other except for being sealed together along the perimeter margin at the lengthwise end of product 10 which provides a tear-off strip 34 beyond a line of tearing 36 and except for being sealed to second burst seal 32 at mouth 38 of dispensing funnel chamber 16 and also being sealed together along the exterior side of the dispensing funnel chamber below mouth 38.

The construction just described results in dispensing funnel chamber 16 being hermetically sealed while first burst pouch 14 is open at the lengthwise end margin of product 10 opposite first burst seal 30 and second burst pouch 18 is open along the right side margin of product 10 as in FIG. 1.

Figure 4:
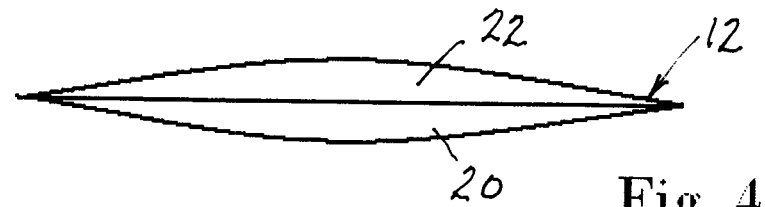
FIG. 4 is a view in the direction of arrows 4-4 in FIG. 3.
Figure 11:
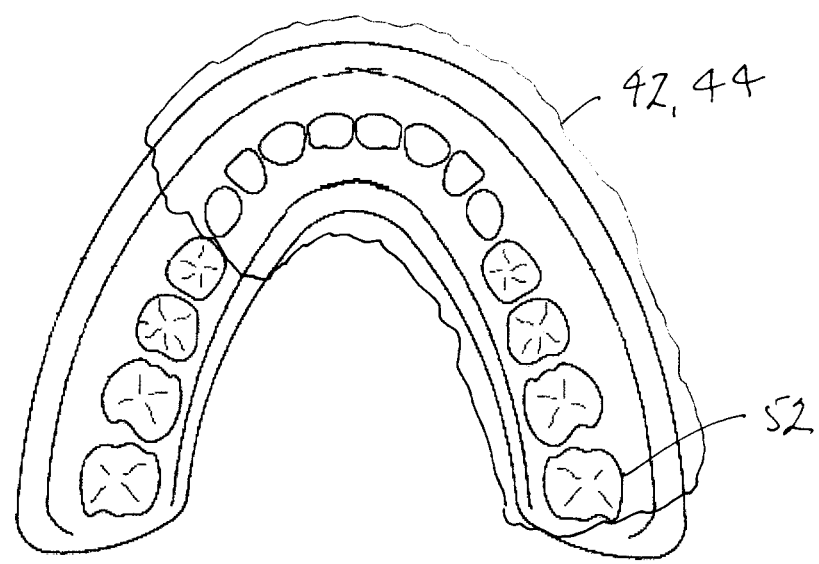
FIGS. 10-11 are views showing how the enclosure is used to fabricate a dental arch model in the impression.
Figure 12:
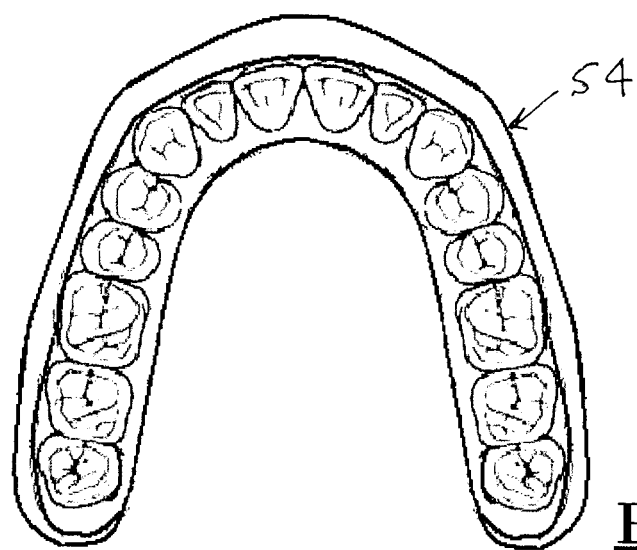
FIG. 12 is a top plan view of the finished dental arch model after having been removed from the impression.

The opening to first burst pouch 14 allows it to be filled with a first monomer 42 (see FIG. 3) after which it is sealed closed by heat sealing the margins of sheets 20 and 22 together between side seal 24 and side seal 28 as indicated by reference numeral 40. This hermetically seals first monomer 42 in first burst pouch 14. The opening to second burst pouch 18 allows it to be filled with a second monomer 44 (see FIG. 3) after which it is sealed closed by heat sealing the margins of sheets 20 and 22 together between side seal 26 and side seal 28 as indicated by reference numeral 46. Filling each burst pouch with a respective monomer will slightly bulge each burst pouch as suggested by FIG. 4.

Figure 5:
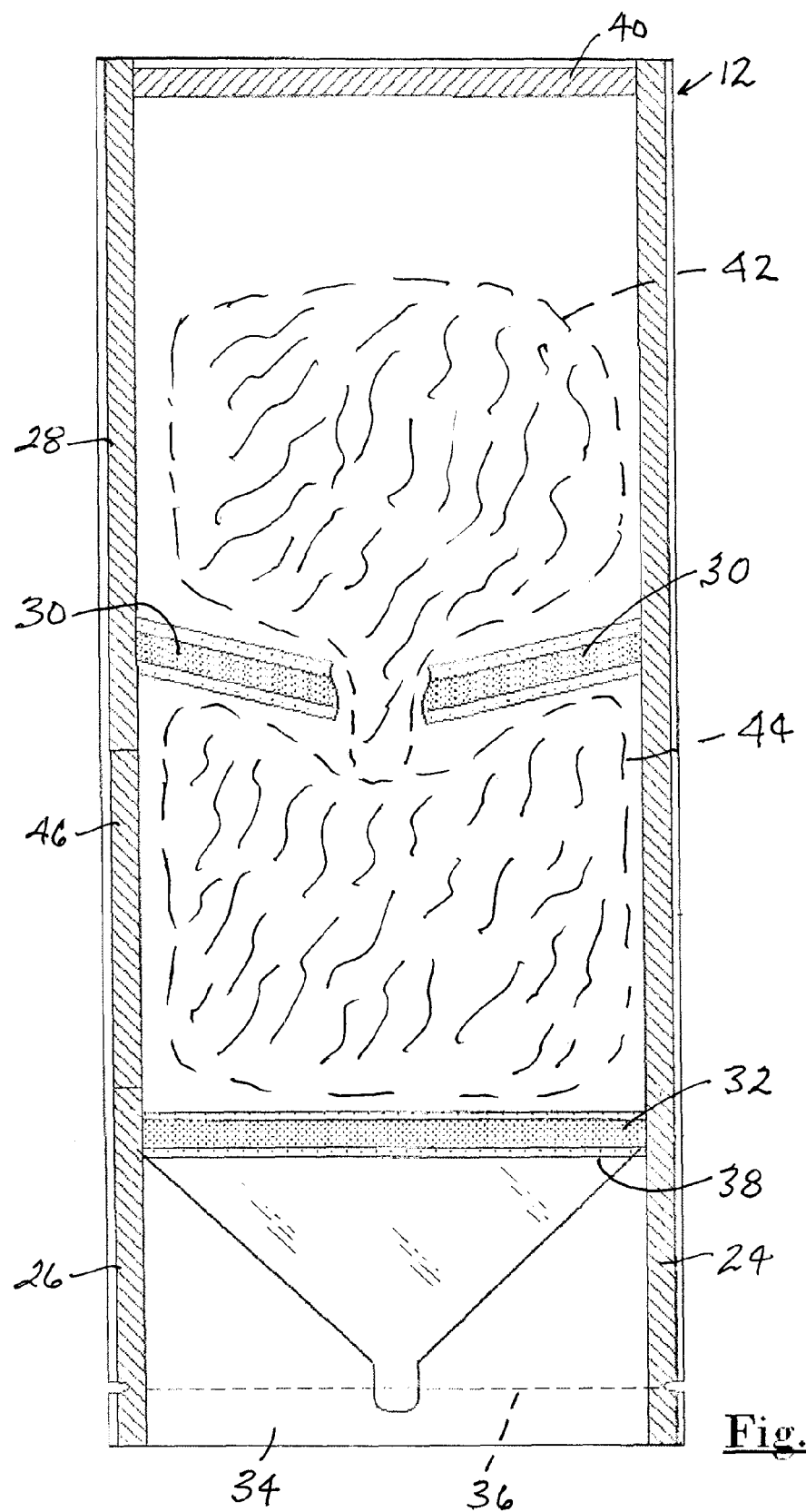
FIGS. 5-8 are a series of steps showing use of the enclosure.

FIGS. 5-8 show a series of steps for using enclosure 12. FIG. 5 shows first burst pouch 14 having been externally squeezed, such as by a person's hand, with sufficient pressure to break first burst seal 30 and begin forcing some of first monomer 42 into second burst pouch 18 thereby initiating the polymerization process. The sheets themselves and the other seals surrounding first burst pouch 14 have greater strength than first burst seal 30 and consequently do not break or rupture. Because sheets 20 and 22 are transparent, a person squeezing the enclosure can observe the monomers beginning to mix.

Figure 6:
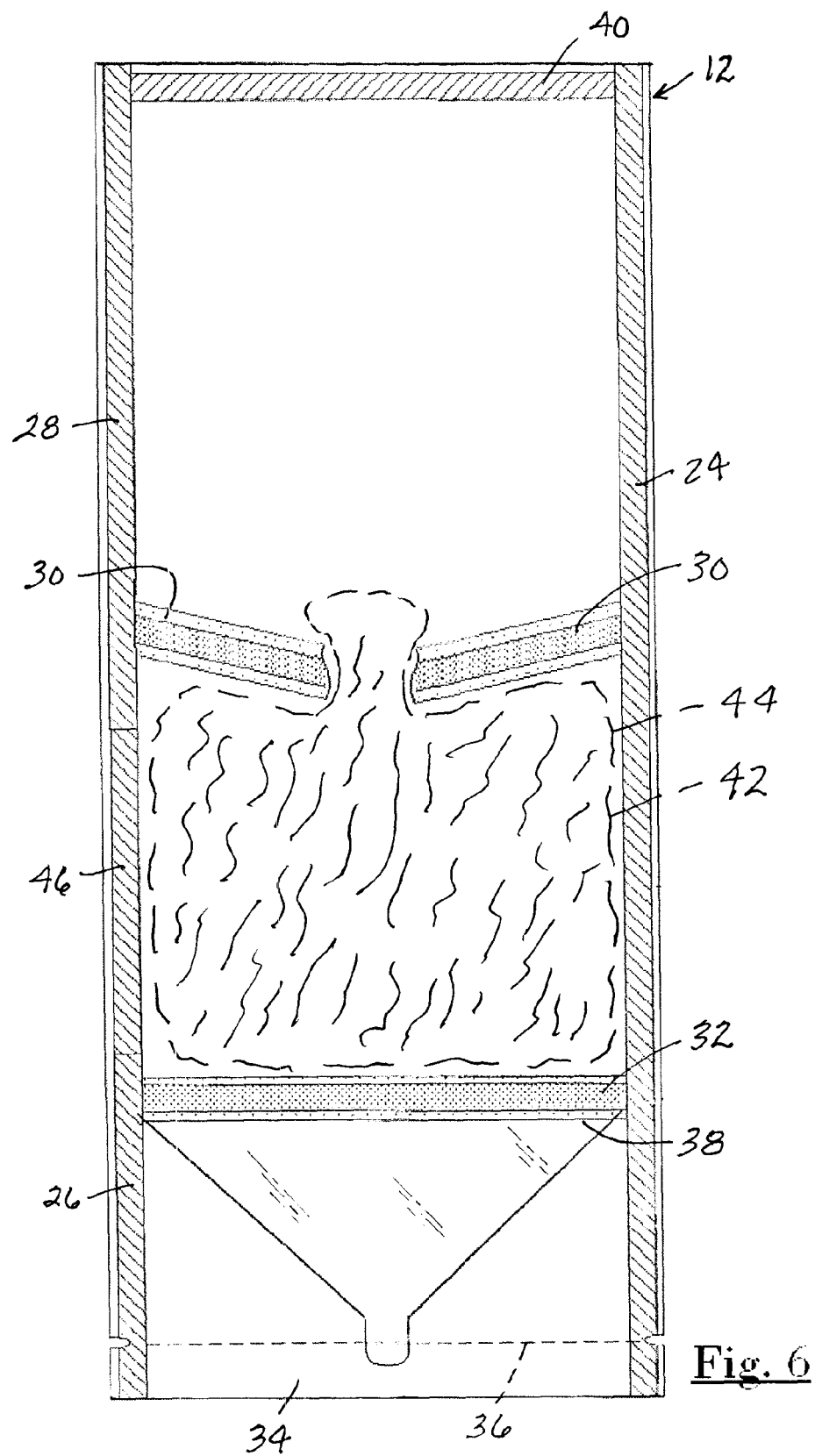

The person can then manipulate and continue to squeeze burst pouches 14 and 18 so as to thoroughly mix the two monomers, while forcing the mixture largely into second burst pouch 18 but without breaking second burst seal 32 as suggested by FIG. 6. The flexibility of sheets 20 and 22 allows first burst pouch 14 to be rolled up in a downward direction in FIG. 6 toward second burst pouch 18 thereby collapsing the first burst pouch as its contents are being forced into the second burst pouch.

Figure 7:
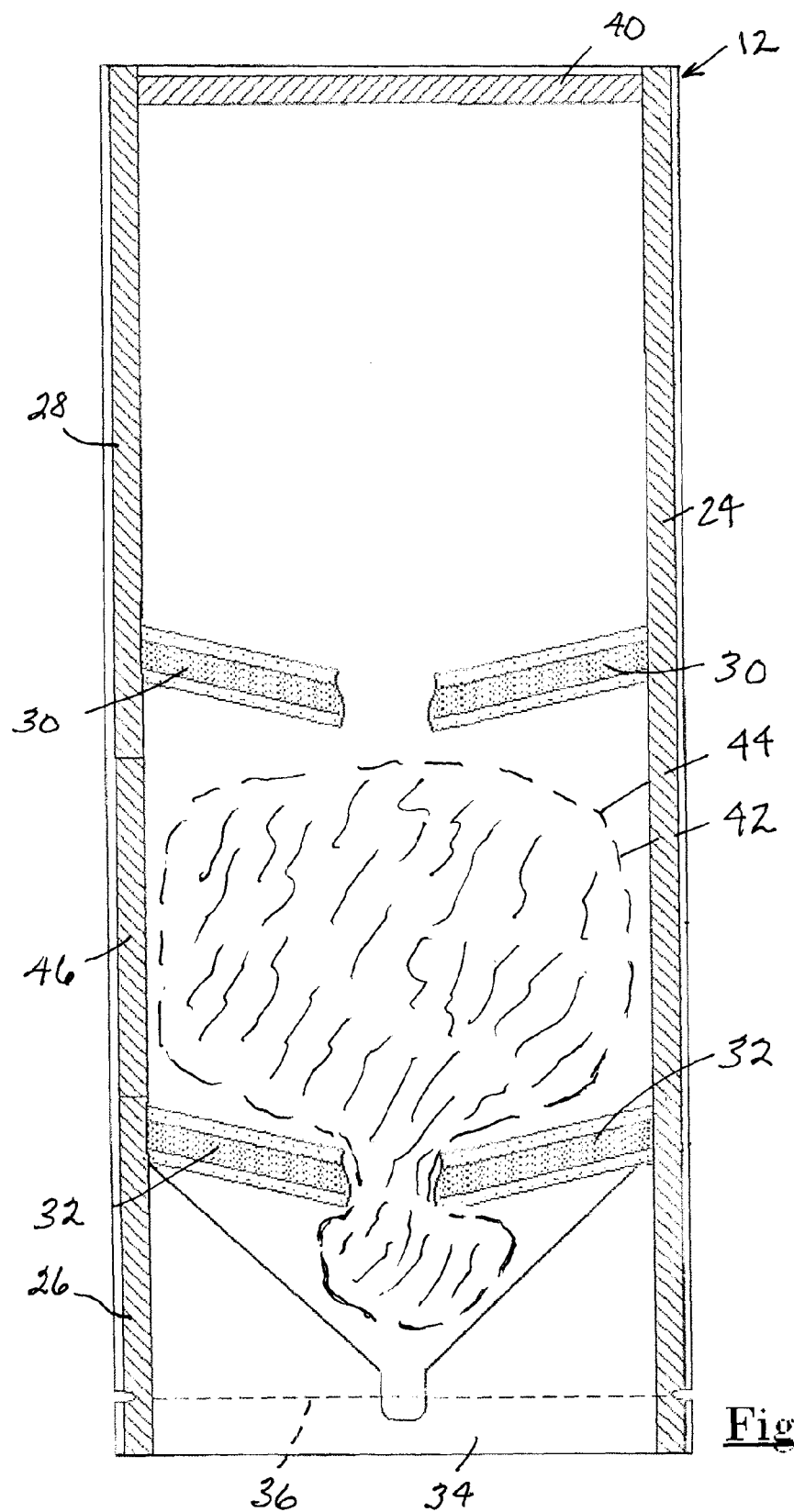

With first burst pouch 14 largely collapsed, increased pressure applied externally to second burst pouch 18 causes second burst seal 32 to break and force at least some of the mixture into dispensing funnel chamber 16 as suggested by FIG. 7. This is done without the sheets and the side seals of second burst pouch 18 rupturing. Enclosure 12 continues to hermetically seal the mixture as the reaction continues.

Figure 8:
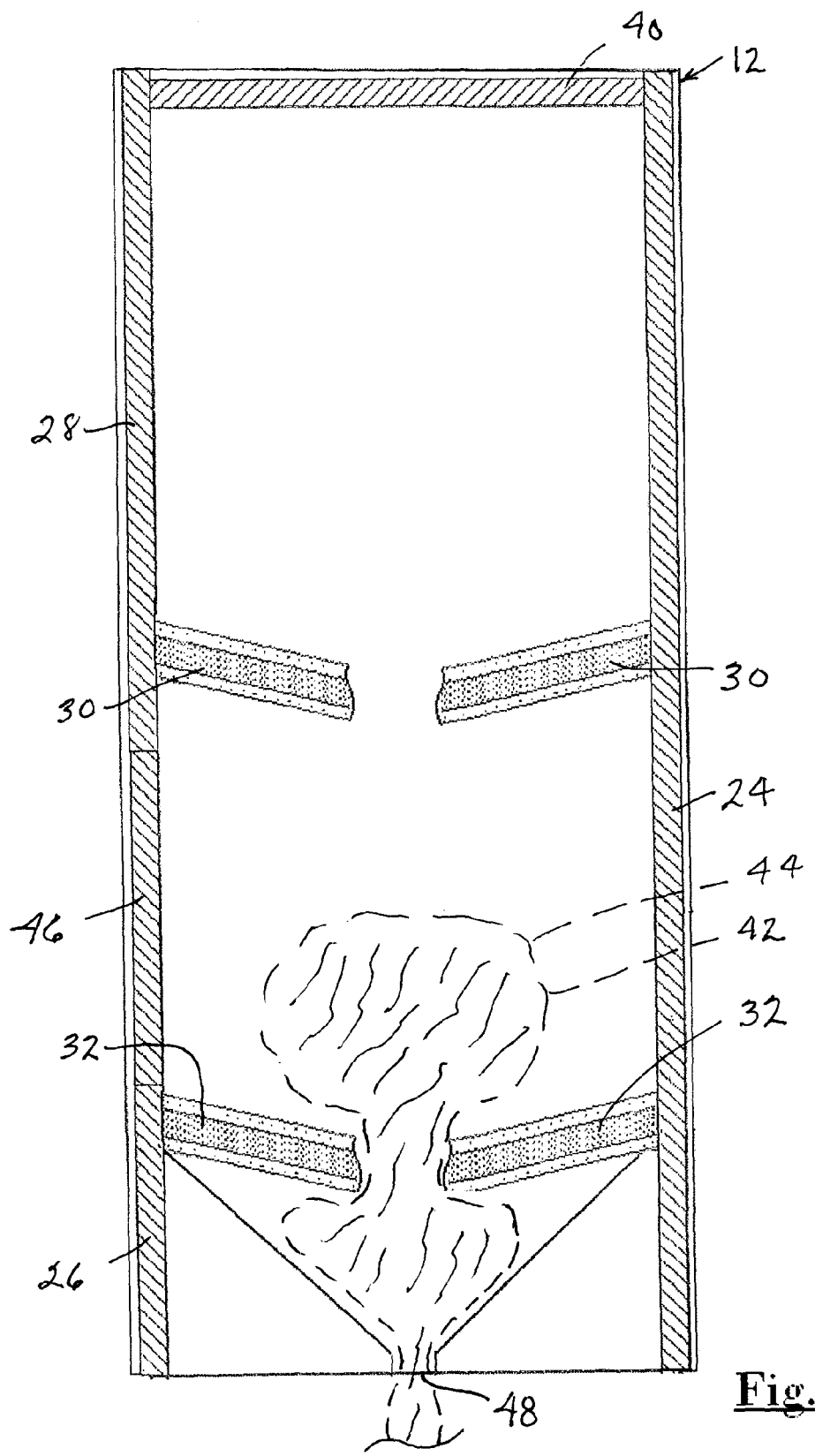

With the mixture having been forced into dispensing funnel chamber 16, tear-off strip 34 is torn off to open an outlet 48 of dispensing funnel chamber 16 as in FIG. 8. Further squeezing of mixture in second burst pouch 18 and dispensing funnel chamber 16 forces mixture out of enclosure 12 through outlet 48. Squeezing is continued until substantially all of the mixture, or a lesser quantity if desired, has been dispensed. When the polymerization process concludes, the dispensed mixture becomes a solid polymer.

Figure 9:
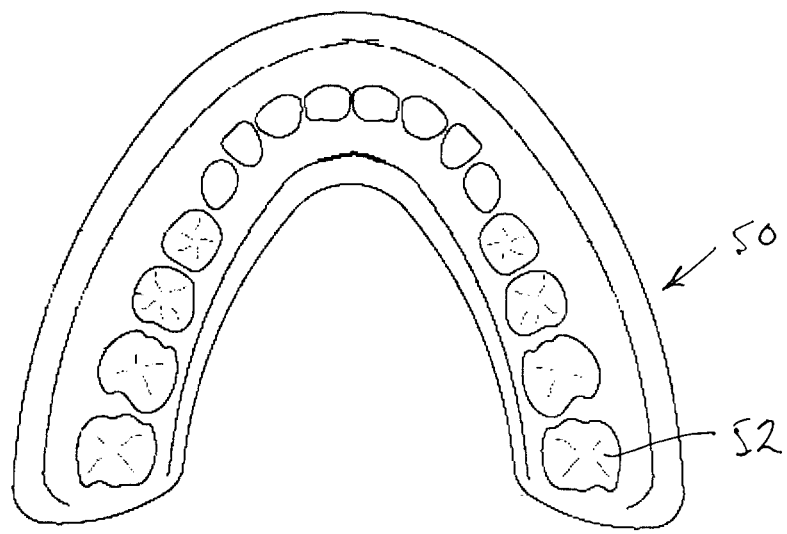
FIG. 9 is a top plan view of an impression of a dental arch.
Figure 10:
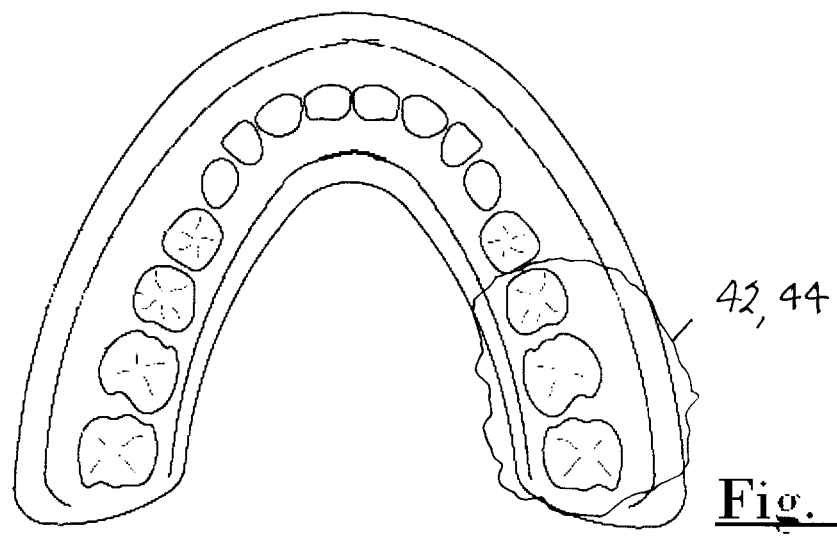

FIGS. 9-12 show an example of using enclosure 12 to fabricate a polyurethane dental arch model. An impression 50 of a person's dental arch is shown in FIG. 9. With tear-off strip 34 having been torn off to open outlet 48, enclosure 12 is positioned over impression 50 with outlet 48 pointed at a molar cavity 52 at one end of the impression. Enclosure 12 is squeezed to force mixture through outlet 48 and into molar cavity 52. A sufficient quantity of mixture is dispensed to completely fill and overflow molar cavity 52 to form margins which can provide a base for the finished arch model. This procedure of filling cavities of impression 50 is continued in succession around the entire arch model as suggested by FIGS. 10 and 11. Because of the limited time before the reaction concludes, the procedure is conducted promptly and without interruption.

During this time the mixture is clear enough for a person to observe any air bubbles with may form in a tooth cavity in the impression, affording the opportunity for the person to puncture an air bubble with a pointed instrument before the reaction concludes.

Conclusion of the reaction can be observed by a sudden change in opaqueness of the mixture as it become solid, such as a transformation from largely clear to white. The polymerized material can then be removed from impression 50 and trimmed as needed to create a finished dental arch model 54 shown in FIG. 12. Impression 50 can be any conventional material used to create an impression of a part of the human body. Such materials have some flexibility which allows them to be pried off the finished model.

The size of product 10 is large enough to contain the quantities of monomers needed for fabricating the dental device or aid intended to be made. For example, the illustrated rectangular shaped product 10 has a length of about 11.00 inch and a width of about 4.25 inch.

Figure 13:
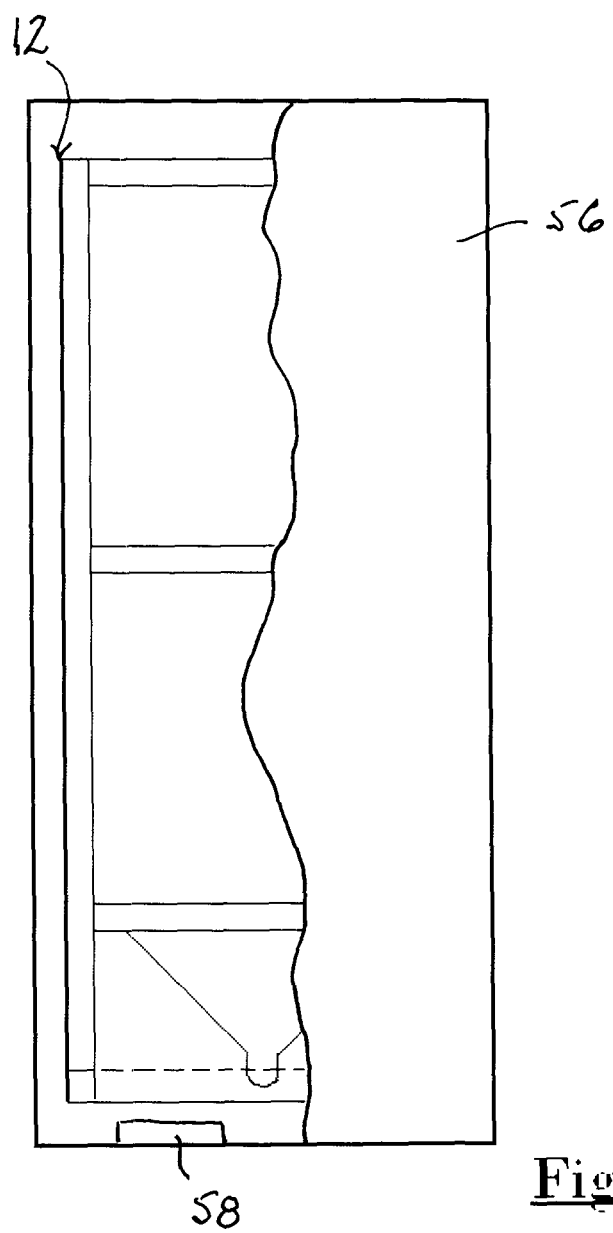
FIG. 13 is a hermetically sealed packaged product containing one or more of the above-described hermetically sealed enclosures.

In order to assure sufficient shelf life for the hermetically sealed enclosure, filling of each burst pouch is conducted in an inert atmosphere, such as nitrogen, to exclude the presence of air in each burst pouch. Additionally, each such enclosure 12 is further packaged in a hermetically sealed container, such as a bag 56 shown in FIG. 13, which is also filled with an inert atmosphere like nitrogen, to exclude the presence of oxygen. Before bag 56 is sealed closed a small desiccant bag 58 is placed inside bag 56 to absorb any moisture which may have accidentally been entrained with the nitrogen. By making bag 56 from a foil, rather than a transparent material like polyethylene, the transparent hermetically sealed enclosures inside the foil bag are protected from exposure to light which otherwise might degrade the monomers in their burst pouches. Multiple enclosures 12 may be packaged in a single bag 56.

What is claimed is:

1. A method of making a hermetically sealed enclosure for use in fabricating a polymeric dental article, the method comprising:

disposing two flexible sheets face-to-face and sealing certain portions together to form a) a first burst pouch at one lengthwise end of the enclosure which is hermetically sealed except along an open portion of a perimeter margin through which the first burst pouch can be filled, b) a hermetically sealed dispensing funnel chamber at an opposite lengthwise end of the enclosure, c) a second burst pouch which is between the first burst pouch and the dispensing funnel chamber and which is hermetically sealed except along an open portion of a perimeter margin through which the second burst pouch can be filled, d) a first burst seal between a lengthwise inner end of the first burst pouch and a first lengthwise end of the second burst pouch adjacent the first burst pouch, e) a second burst seal disposed between a second lengthwise end of the second burst pouch and an inner lengthwise end of the dispensing funnel chamber which is adjacent the second lengthwise end of the second burst pouch, and f) a tear-off strip closing an outlet of the dispensing funnel chamber at an outer lengthwise end of the dispensing funnel chamber;

then, after the first burst pouch, the dispensing funnel chamber, the second burst pouch, the first burst seal, the second burst seal, and the tear-off strip have been formed, filling the first burst pouch through the open portion of its perimeter margin with a first monomer and then hermetically sealing its open perimeter margin closed; and filling the second burst pouch through the open portion of its perimeter margin with a second monomer and then hermetically sealing its open perimeter margin closed.

2. A method as set forth in claim 1 including filling a portion of the first burst pouch which is not occupied by the first monomer with nitrogen gas to exclude air from the first burst pouch before hermetically sealing the open portion of its perimeter margin closed and filling a portion of the second burst pouch which is not occupied by the second monomer with nitrogen gas to exclude air from the second burst pouch before hermetically sealing the open portion of its perimeter margin closed.

3. A method as set forth in claim 2 further comprising enclosing the enclosure in a hermetically sealed container containing a nitrogen atmosphere which is free of air.

4. A method as set forth in claim 3 further comprising also enclosing a desiccant bag in the hermetically sealed container.

5. A method as set forth in claim 2 further comprising enclosing the enclosure in a hermetically sealed container which blocks passage of outside light into the container.

6. A method as set forth in claim 1 in which the filling of the second burst pouch through the open portion of its perimeter margin with a second monomer comprises filling the open portion of its perimeter margin with a second monomer through an open portion of a side margin of the second burst pouch.

7. A method as set forth in claim 6 in which the filling of the first burst pouch through the open portion of its perimeter margin with a first monomer comprises filling the open portion of its perimeter margin with a first monomer through an open portion of an end margin of the first burst pouch.

* * * * *